United States Patent
Yakubo et al.

(10) Patent No.: US 11,254,583 B2
(45) Date of Patent: *Feb. 22, 2022

(54) TITANIUM OXIDE POWDER, AND DISPERSION AND COSMETIC USING SAID POWDER

(71) Applicant: SUMITOMO OSAKA CEMENT CO., LTD., Tokyo (JP)

(72) Inventors: Teppei Yakubo, Tokyo (JP); Tsutomu Nozoe, Tokyo (JP); Tetsuro Itagaki, Tokyo (JP)

(73) Assignee: SUMITOMO OSAKA CEMENT CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/957,376

(22) PCT Filed: Dec. 27, 2018

(86) PCT No.: PCT/JP2018/048124
§ 371 (c)(1),
(2) Date: Jun. 23, 2020

(87) PCT Pub. No.: WO2019/131871
PCT Pub. Date: Jul. 4, 2019

(65) Prior Publication Data
US 2020/0325034 A1    Oct. 15, 2020

(30) Foreign Application Priority Data
Dec. 28, 2017    (JP) .............................. JP2017-253644

(51) Int. Cl.
*C01G 23/047*    (2006.01)
*A61K 8/04*    (2006.01)
*A61K 8/29*    (2006.01)

(52) U.S. Cl.
CPC .............. *C01G 23/047* (2013.01); *A61K 8/04* (2013.01); *A61K 8/29* (2013.01); *C01P 2004/41* (2013.01);
(Continued)

(58) Field of Classification Search
None
See application file for complete search history.

(56) References Cited

U.S. PATENT DOCUMENTS 9,505,630 B2 * 11/2016 Lee .......................... B01J 37/10
10,717,658 B2 * 7/2020 Yakubo .................. A61K 8/044
2019/0161360 A1 * 5/2019 Yakubo ................ A61K 8/0245

FOREIGN PATENT DOCUMENTS

CN    102849793 A   *   1/2013
JP    2007106646 A   *   4/2007
(Continued)

OTHER PUBLICATIONS

Dictionary.com. "Powder." https://www.dictionary.com/browse/powderaccessed Aug. 9, 2021, pp. 1-7. (Year: 2021).*
(Continued)

*Primary Examiner* — Isaac Shomer
(74) *Attorney, Agent, or Firm* — JCIPRNET

(57) ABSTRACT

A titanium oxide powder of the present invention has a BET specific surface area of 5 $m^2/g$ or more and 15 $m^2/g$ or less and contains polyhedral-shaped titanium oxide particles having eight or more faces, in which a mass reduction rate in a case of being heated at 800° C. for 1 hour in an air atmosphere is 0.03% by mass or more and 0.5% by mass or less.

9 Claims, 4 Drawing Sheets

(52) U.S. Cl.
CPC ...... *C01P 2004/51* (2013.01); *C01P 2004/60* (2013.01); *C01P 2006/12* (2013.01)

(56) References Cited

FOREIGN PATENT DOCUMENTS

| | | | |
|---|---|---|---|
| JP | 2013028563 | 2/2013 | |
| JP | 2014015340 | 1/2014 | |
| WO | 2018003851 | 1/2018 | |
| WO | WO-2018003851 A * | 1/2018 | ............. A61K 8/044 |

OTHER PUBLICATIONS

Google Patents. English Translation of CN 102849793 A. https://patents.google.com/patent/CN102849793A/en?oq=CN+102849793 accessed May 21, 2021, originally published Jan. 2, 2013, pp. 1-8. (Year: 2013).*

D. P. Romanov and V. N. Skrobot. "Distortions of Octahedra in Rutile-Type Structures of Transition Element Dioxides." Glass Physics and Chemistry, 2009, vol. 35, No. 5, pp. 518-524. (Year: 2009).*

Ligang Gai, Qinghu Mei, Xuyang Qin, Wenpeng Li, Haihui Jiang, Xiuquan Duan. "Controlled synthesis of anatase $TiO_2$ octahedra with enhanced photocatalytic activity." Materials Research Bulletin 48 (2013) 4469-4475. (Year: 2013).*

Google Patents. English Translation of JP2007106646A. Available as of https://patents.google.com/patent/JP2007106646A/en on Oct. 16, 2020, originally published in Japanese on Apr. 26, 2007, pp. 1-8. (Year: 2007).*

Google Patents. https://patents.google.com/patent/JPW02019131871A1/en accessed from web on Nov. 29, 2021, originally published on Dec. 24, 2020, originally filed in Japanese on Dec. 28, 2017, pp. 1-14. (Year: 2020).*

"International Search Report (Form PCT/ISA/210) of PCT/JP2018/048124", dated Feb. 26, 2019, with English translation thereof, pp. 1-4.

* cited by examiner ical PCT application serial no. PCT/JP2018/048124, filed on
TITANIUM OXIDE POWDER, AND DISPERSION AND COSMETIC USING SAID POWDER

CROSS-REFERENCE TO RELATED APPLICATION

This application is a 371 application of an international PCT application serial no. PCT/JP2018/048124, filed on Dec. 27, 2018, which claims the priority benefit of Japan application JP2017-253644, filed on Dec. 28, 2017. The entirety of the abovementioned patent application is hereby incorporated by reference herein and made a part of this specification.

TECHNICAL FIELD

The present invention relates to a titanium oxide powder suitable for cosmetics, and a dispersion and cosmetics using the same.

Priority is claimed on Japanese Patent Application No. 2017-253644, filed on Dec. 28, 2017, the content of which is incorporated herein by reference.

BACKGROUND ART

Titanium oxide particles have excellent light reflection characteristics, ultraviolet ray shielding characteristics, and a concealing ability. Therefore, titanium oxide particles having submicron size to micron size are used for base makeup cosmetics such as foundations.

As titanium oxide particles suitable for cosmetics, for example, spherical anatase-type titanium oxide particles having an average particle diameter of 0.1 µm to 5 µm have been proposed (for example, see Patent Literature 1).

In addition, spherical rutile-type titanium oxide particles obtained by accumulating spherical primary particles and having an apparent average particle diameter of 100 nm or higher have also been proposed (for example, see Patent Literature 2).

CITATION LIST

Patent Literature

[Patent Literature No. 1] Japanese Laid-open Patent Publication No. 2013-28563

[Patent Literature No. 2] Japanese Laid-open Patent Publication No. 2014-15340

SUMMARY OF INVENTION

Technical Problem

However, there is a requirement of further improvement for titanium oxide particles capable of decreasing paleness peculiar to titanium oxide particles while having a concealing ability and a feeling of transparency. Furthermore, in a case of being applied to the skin, there is a requirement for titanium oxide particles having excellent spreadability on the skin and excellent high adhesion to the skin.

The present invention has been made in view of the above circumstances, and an object of the present invention is to provide a titanium oxide powder which can decrease paleness peculiar to titanium oxide particles while having a concealing ability and a feeling of transparency in a case of being applied to the skin and which have excellent spreadability on the skin and excellent high adhesion to the skin, and a dispersion and cosmetics using the same.

Solution to Problem

That is, the titanium oxide powder of the present invention is a titanium oxide powder having a BET specific surface area of 5 $m^2/g$ or more and 15 $m^2/g$ or less, and containing polyhedral-shaped titanium oxide particles having eight or more faces, in which a mass reduction rate in a case of being heated at 800° C. for 1 hour in an air atmosphere is 0.03% by mass or more and 0.5% by mass or less.

The dispersion of the present invention includes the titanium oxide powder of the present invention and a dispersion medium.

The cosmetics of the present invention contain the titanium oxide powder of the present invention and a cosmetic base.

Advantageous Effects of Invention

According to the titanium oxide powder of the present invention, it is possible to provide a titanium oxide powder which can decrease paleness peculiar to titanium oxide particles while having a concealing ability and a feeling of transparency in a case of being applied to the skin and which have excellent spreadability on the skin and excellent high adhesion to the skin, and a dispersion and cosmetics using the same.

According to the dispersion of the present invention, in a case where cosmetics containing the dispersion are applied to the skin, it is possible to decrease paleness peculiar to titanium oxide particles while having a concealing ability and a feeling of transparency, spreadability on the skin is excellent, and adhesion to the skin is excellent.

According to the cosmetics of the present invention, it is possible to decrease paleness peculiar to titanium oxide particles while having a concealing ability and a feeling of transparency in a case of being applied to the skin, spreadability on the skin is excellent, and adhesion to the skin is excellent.

DESCRIPTION OF EMBODIMENTS

Figure 1:
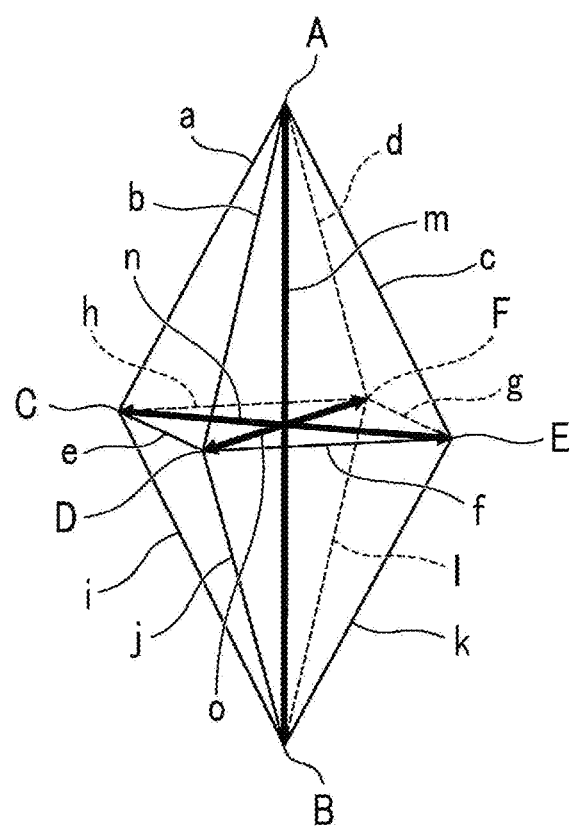
FIG. 1 is a schematic diagram showing a preferred example of octahedral-shaped titanium oxide particles.

Preferred embodiments of a titanium oxide powder of the present invention, and a dispersion and cosmetics using the same will be described.

The present embodiments will be described in detail in order to better understand the gist of the invention, and the present invention is not limited unless otherwise specified. Omissions, additions, substitutions, and other changes can be made without departing from the gist of the present invention.

[Titanium Oxide Powder]

A titanium oxide powder of the present embodiment has a BET specific surface area of 5 m$^2$/g or more and 15 m$^2$/g or less and contains polyhedral-shaped titanium oxide particles having eight or more faces, in which a mass reduction rate in a case of being heated at 800° C. for 1 hour in an air atmosphere is 0.03% by mass or more and 0.5% by mass or less.

(Specific Surface Area)

A BET specific surface area of the titanium oxide powder of the present embodiment is 5 m$^2$/g or more and 15 m$^2$/g or less, and preferably 5 m$^2$/g or more and 13 m$^2$/g or less.

A case where the BET specific surface area of the titanium oxide powder is 5 m$^2$/g or more and 15 m$^2$/g or less is advantageous from the viewpoint of further decreasing paleness peculiar to titanium oxide particles while having a concealing ability and a feeling of transparency. Furthermore, in a case where the BET specific surface area of the titanium oxide powder is less than 5 m$^2$/g, a feeling of transparency is deteriorated due to light scattering. On the other hand, in a case where the BET specific surface area of the titanium oxide powder is greater than 15 m$^2$/g, scattering intensity of light having a short wavelength increases as compared with scattering intensity of light having a long wavelength, and thus paleness increases.

As a method of measuring the BET specific surface area, for example, a method of performing measurement from a nitrogen adsorption isotherm by the BET multipoint method using a fully automated specific surface area measuring device (trade name: BELSORP-Mini II, manufactured by MicrotracBEL Corp.) is mentioned.

A mass reduction rate of the titanium oxide powder of the present embodiment in a case of being heated at 800° C. for 1 hour in an air atmosphere is 0.03% by mass or more and 0.5% by mass or less. In addition, any mass reduction rate can be selected as necessary, as long as the mass reduction rate is within the above range. The mass reduction rate may be 0.03% to 0.10% by mass, 0.03% to 0.09% by mass, 0.03% to 0.15% by mass, 0.15% to 0.25% by mass, 0.25% to 0.35% by mass, or 0.35% to 0.50% by mass.

By setting the mass reduction rate to be within the above range, adhesion to the skin in a case where cosmetics containing the titanium oxide powder of the present embodiment are applied to the skin is improved. In addition, in a case where the mass reduction rate is less than 0.03% by mass, adhesion of the cosmetics in a case of being applied to the skin decreases. On the other hand, in a case where the mass reduction rate is greater than 0.5% by mass, the interaction between particles increases, and spreadability of the powder in a case of being applied is deteriorated.

It is presumed that density of hydroxyl groups on surfaces of titanium oxide particles needs to be a certain value or higher in order to improve adhesion of the cosmetics containing the titanium oxide powder to the skin. It is known that in a case where the hydroxyl groups existing on the surfaces of titanium oxide particles are heated, two adjacent hydroxyl groups react with each other to generate water and are desorbed from the titanium oxide powder as water. It may be considered that a mass reduction amount of the titanium oxide powder of the present embodiment indicates the mass of water desorbed from the titanium oxide powder.

Therefore, the density of the hydroxyl groups existing on the surface of the titanium oxide particles can be quantified by heating at 800° C., which is a temperature required for desorption of water, for 1 hour.

As described in Patent Literature 1, in the titanium oxide powder produced by calcination at 600° C. to 800° C., a mass reduction rate in a case of being heated at 800° C. for 1 hour (hereinafter, referred to as a "mass reduction rate" in some cases) is 0.02% by mass or less. On the other hand, a mass reduction rate of the titanium oxide powder of the present embodiment is 0.03% by mass or more, and therefore adhesion of the cosmetics containing the titanium oxide powder to the skin can be improved.

In addition, by setting the mass reduction rate to be within the above range, the hydroxyl groups appropriately existing on the surface of each particle of the titanium oxide powder improve compatibility with the skin, and thus spreadability can be improved.

[Titanium Oxide Particles]

The titanium oxide powder of the present embodiment is an agglomerate of titanium oxide particles.

A shape of each of the titanium oxide particles of the present embodiment is a polyhedral shape having eight or more faces.

The shape of each of the titanium oxide particles is a shape having eight or more faces, whereby light can be scattered over a wide range. Therefore, when the cosmetics containing the titanium oxide powder is applied to the skin, a feeling of transparency and a concealing ability can be improved.

An amount of polyhedral-shaped titanium oxide particles having eight or more faces in the titanium oxide powder is represented by % by number calculated by a method described later. That is, the amount of polyhedral-shaped titanium oxide particles having eight or more faces in the titanium oxide powder is preferably 50% by number or more, may be 60% by number or more, or may be 70% by number or more. The upper limit of the amount of polyhedral-shaped titanium oxide particles having eight or more faces in the titanium oxide powder may be 80% by number, may be 90% by number, or may be 100% by number.

A case where the amount of the polyhedral-shaped titanium oxide particles having eight or more faces in the titanium oxide powder is 50% by number or more is advantageous from the viewpoint of further decreasing paleness peculiar to titanium oxide particles while having an excellent concealing ability and a feeling of transparency in a case where cosmetics containing a titanium oxide powder are applied to the skin.

An amount of the polyhedral-shaped titanium oxide particles having eight or more faces in the titanium oxide powder, that is, % by number can be calculated by, for example, observing 100 titanium oxide particles with a scanning electron microscope (SEM) and counting the number of polyhedral-shaped titanium oxide particles having eight or more faces included in the 100 particles.

Each particle of the titanium oxide particles has line segments each of which connects two apexes which face each other and has a maximum value of the line segments, and an average value of the maximum values is preferably 100 nm or higher and 1000 nm or lower, more preferably 150 nm or higher and 800 nm or lower, and even more preferably 200 nm or higher and 750 nm or lower. The two apexes which face each other are not adjacent to each other. That is, in the two apexes, the line connecting the apexes is a line that does not pass through the surface of the particle but passes through the inside of the particle. The maximum value is obtained by a combination of apexes that are farthest from each other.

Any polyhedral shape having eight or more faces can be selected. A particle having a polyhedral shape is a particle having a plurality of faces. For example, shapes such as an octahedral shape, a decahedral shape, a dodecahedral shape, an icosahedral shape, and a star shape are mentioned. Respective faces of the polyhedral shape may be substantially the same, or may be faces having a plurality of different shapes from each other, such as two types. The polyhedral shape may be a regular polyhedral shape or may be another polyhedral shape. As specific examples, shapes such as a regular octahedron and a rectangular bipyramid are mentioned. Among these, octahedral-shaped titanium oxide particles are preferable from the viewpoint that light can be scattered over a wide range.

Hereinafter, octahedral-shaped titanium oxide particles will be described in detail as a preferred example of the present invention.

(Octahedral-Shaped Titanium Oxide Particles)

An octahedral shape described below is a three-dimensional shape in which an internal space is surrounded by eight triangles, as shown in FIG. 1. The eight triangles may all have the same shape, or may have two or more different shapes including shapes of two different types.

A tip end part of the respective apexes of the octahedral-shaped titanium oxide particles (points indicated by reference signs A, B, C, D, E, and F in FIG. 1) may have a sharp shape, a rounded shape, or a flat shape.

In the titanium oxide powder of the present embodiment, an amount of the octahedral-shaped titanium oxide particles (hereinafter, referred to as an "octahedral-shaped particles" in some cases) is preferably 50% by number or more, may be 60% by number or more, or may be 70% by number or more.

In the titanium oxide powder of the present embodiment, an upper limit of the amount of octahedral-shaped particles may be 80% by number or more, may be 90% by number or more, or may be 100% by number or more.

A case where the amount of the octahedral-shaped particles in the titanium oxide powder is 50% by number or more is advantageous from the viewpoint of further decreasing paleness peculiar to titanium oxide particles while having an excellent concealing ability and a feeling of transparency in a case where cosmetics containing titanium oxide powder are applied to the skin.

The amount of the octahedral-shaped particles in the titanium oxide powder can be calculated, for example, by observing 100 titanium oxide particles with a scanning electron microscope and counting the number of octahedral-shaped particles included in the 100 particles.

(Line Segment which Connects Two Apexes which Face Each Other)

The octahedral-shaped particle has line segments each of which connects two apexes which face each other (hereinafter, referred to as "distances between apexes" or "distances between two apexes which face each other" in some cases) and has a maximum value of the line segments, and an average value of the maximum values is preferably 300 nm or higher and 1000 nm or lower, more preferably 320 nm or higher and 900 nm or lower, even more preferably 330 nm or higher and 800 nm or lower, and most preferably 340 nm or higher and 750 nm or lower.

The average value of the maximum values means an average value obtained from maximum values of a plurality of octahedral-shaped titanium oxide particles in a case where one octahedral-shaped titanium oxide particle has a plurality of line segments each of which connects two apexes which face each other and has a maximum value of lengths thereof. In addition, the line segment connecting two apexes which face each other exists inside the particle but not a surface of the particle.

The octahedral-shaped particle, which has distances between two apexes which face each other and has a maximum value of the distances and in which an average value of the maximum values is 300 nm or higher and 1000 nm or lower, is capable of scattering visible light over a wide range as compared with spherical-shaped titanium oxide particles and spindle-shaped titanium oxide particles. Therefore, it is presumed that cosmetics which contain a titanium oxide powder including the octahedral-shaped particles are capable of decreasing paleness peculiar to titanium oxide particles while achieving both a concealing ability and a feeling of transparency.

A case where the octahedral-shaped particle has distances between two apexes which face each other and has a maximum value of the distances, and an average value of the maximum values is 300 nm or higher and 1000 nm or lower is advantageous from the viewpoint of further decreasing paleness peculiar to titanium oxide particles while having an excellent feeling of transparency in a case of being applied to the skin.

In a case where the octahedral-shaped particle has distances between two apexes which face each other and has a maximum value of the distances, and an average value of the maximum values is 300 nm or higher, light having a short wavelength is hardly scattered and a pale color is suppressed, that is, paleness peculiar to titanium oxide particles can be decreased, which is preferable. On the other hand, in a case where each particle of the octahedral-shaped particles has distances between two apexes which face each other and has a maximum value of the distances, and an average value of the maximum values is 1000 nm or lower, an excellent feeling of transparency is obtained, which is preferable.

A maximum value of distances between two apexes which face each other in the octahedral-shaped particle is measured by observing the octahedral-shaped particles with a scanning electron microscope (SEM). Specifically, with respect to 100 octahedral-shaped particles, the maximum value of the distances between two apexes which face each other in each particle is measured, and the value obtained by arithmetically averaging the plurality of obtained measured values is an average value of the maximum values of the distances between two apexes which face each other.

Here, in a case where the octahedral-shaped particles are not agglomerated with one another as in the present invention, distances between apexes in one octahedral-shaped particle, that is, distances between apexes in a primary particle are measured. On the other hand, in a case of comparing the embodiment of the present invention with other cases in which particles are agglomerated with one another to form agglomerated particles, distances between apexes in the agglomerated particles, that is, distances between apexes in a secondary particle are measured. As examples of the agglomerated particles, agglomerated particles in which particles are agglomerated with one another to form octahedral-shaped agglomerates, agglomerated particles in which octahedral-shaped particles are agglomerated with one another, and the like are mentioned. The same applies to the measurement of the maximum value (X) and the minimum value (Y) described later.

In a case where a tip end part of the apexes of the octahedral-shaped particles is a flat surface, the maximum value of the distances between two apexes which face each other is measured by using a center point of the flat surface as the apex.

The octahedral-shaped particle has line segments each of which connects two apexes which face each other and has a maximum value of lengths of the line segments, and the maximum value, for example, the maximum value of lengths of the line segments (a long axis m of the octahedral-shaped particle shown in FIG. 1) each of which connects two apexes which face each other (points A and B shown in FIG. 1) is denoted by X (nm). On the other hand, a minimum value of lengths of the line segments each of which connects two apexes which face each other, for example, a minimum value of lengths of line segments (a long axis m of the octahedral-shaped particle shown in FIG. 1) each of which is orthogonal to or substantially orthogonal to the line segments (a long axis m of the octahedral-shaped particle shown in FIG. 1) related with the maximum value and each of which connects two apexes which face each other (points C and E or points D and F shown in FIG. 1) in the octahedral-shaped particle is denoted by Y (nm). At this time, an average value of ratios of X to Y (X/Y) is preferably 1.5 or higher and 3.0 or lower, and more preferably 1.5 or higher and 2.5 or lower.

A case where the average value of the ratios (X/Y) is 1.5 or higher and 3.0 or lower is advantageous from the viewpoint that cosmetics which contain a titanium oxide powder including the octahedral-shaped particles are capable of obtaining a light scattering effect of the octahedral-shaped particles in a more effective manner and of further improving a feeling of transparency in a case of being applied to the skin.

Being substantially orthogonal as described above indicates that two line segments (a long axis and a short axis of the octahedral-shaped particles) intersect at an angle of 70° to 90°. In addition, regarding being substantially orthogonal as described above, two line segments (the long axis and the short axis of the octahedral-shaped particles) may be close to each other and intersect each other, or two line segments (the long axis and the short axis of the octahedral-shaped particles) may not necessarily have an intersection point.

An octahedral shape is preferably a rectangular bipyramidal shape in which two rectangular pyramids share a rectangular bottom surface. The octahedral shape in the present embodiment is preferably a shape in which two congruent rectangular pyramids share a rectangular bottom surface, and more preferably a shape in which two congruent rectangular pyramids share a square bottom surface. A tip end part of the rectangular bipyramid may have a sharp shape, a rounded shape, or a flat shape. In addition, in an example of the present embodiment, a side surface shape of the rectangular pyramid is an isosceles triangle, not an equilateral triangle. It is preferable that the side surface shape is an isosceles triangle. The maximum value (X) of distances between two apexes which face each other in the octahedral-shaped particle means a length of a line segment that gives a distance between two apexes present in a direction orthogonal with respect to the bottom surface of the rectangular pyramids. In addition, the minimum value (Y) of distances between two apexes which face each other in the octahedral-shaped particle means a length of a shorter diagonal line in two diagonal lines on the bottom surface of the two rectangular pyramids.

Here, the distance between two apexes will be described with reference to the drawings. FIG. 1 is a schematic diagram showing a preferred example of octahedral-shaped titanium oxide particles in the titanium oxide particles of the present embodiment. With regard to a plurality of apexes included in each particle of the octahedral-shaped particles, as distances between two apexes, there are a total 15 distances of a distance a between points A and C, a distance b between points A and D, a distance c between points A and E, a distance d between points A and F, a distance e between points C and D, a distance f between the points D and E, a distance g between points E and F, a distance h between points F and C, a distance i between points B and C, a distance j between points B and D, a distance k between points B and E, a distance l between points B and F, a distance n between points C and E, a distance o between points D and F, and a distance m between points A and B, as shown in FIG. 1. In FIG. 1, as distances between two apexes which face each other in the octahedral-shaped particle, there are 3 distances of the distance n between points C and E, the distance o between points D and F, and the distance m between points A and B. A maximum value of the distances between two apexes which face each other in the octahedral-shaped particle is the distance m, which corresponds to the maximum value (X) of the distances between two apexes which face each other in the octahedral-shaped particle. In addition, in FIG. 1, line segments each of which is substantially orthogonal to a line segment which corresponds to the maximum value X, and each of which connects two apexes which face each other in the octahedral-shaped particle are the distance n and the distance o. In the distance n and the distance o, a shorter distance corresponds to the minimum value (Y) of the distances between two apexes which face each other in the octahedral-shaped particle.

The maximum value (X) (nm) of the distances between two apexes which face each other in the octahedral-shaped particle, and the minimum value (Y) (nm) of the distances between two apexes which face each other in the octahedral-shaped particle can be measured, for example, by observing the octahedral-shaped particles using a scanning electron microscope (SEM).

The above ratio (X/Y) is calculated by observing the titanium oxide particles with a scanning electron microscope (SEM) and measuring the maximum value (X) and the minimum value (Y). The value obtained by calculating the ratios (X/Y) for the 100 octahedral-shaped titanium oxide particles, respectively, and arithmetically averaging the obtained plurality of values is an average value of the above ratios (X/Y).

(Average Particle Diameter Converted from BET Specific Surface Area)

An average particle diameter (hereinafter also referred to as "BET-converted average particle diameter") of the titanium oxide powder which is converted from a BET specific surface area of the titanium oxide powder is preferably 300 nm or higher and 1000 nm or lower, more preferably 310 nm or higher and 800 nm or lower, and even more preferably 320 nm or higher and 700 nm or lower.

The BET-converted average particle diameter of the titanium oxide powder can be calculated by Expression (1) in a case where the titanium oxide particles have an octahedral shape.

$$\text{BET-converted average particle diameter (nm)} = 16240/(\text{BET specific surface area } (m^2/g) \times \rho \, (g/cm^3)) \quad (1)$$

In Expression (1), $\rho$ represents a density of the titanium oxide.

Even in a case where the titanium oxide powder contains titanium oxide particles having a shape other than octahedral-shaped particles, the BET-converted average particle diameter is calculated by using Expression (1) in a case where the octahedral-shaped particles of 50% by number or more are contained in the titanium oxide powder.

(Average Value of Maximum Values/BET-Converted Average Particle Diameter)

A value (average value of maximum values/BET-converted average particle diameter) obtained by dividing the average value of the maximum values by the average particle diameter of the octahedral-shaped particles which is converted from the BET specific surface area is preferably 0.5 or higher and 2.5 or lower, more preferably 0.7 or higher and 1.4 or lower, and even more preferably 0.9 or higher and 1.3 or lower.

In a case where (the average value of the maximum values/the BET-converted average particle diameter) is lower than 0.5, it is assumed that fine pores and the like are present in the titanium oxide particles, a refractive index as particles is lower than an original value of titanium oxide particles, which may, as a result, decrease a concealing ability. On the other hand, in a case where (the average value of the maximum values/the BET-converted average particle diameter) is 2.5 or lower, in a case of applying cosmetics which contain the titanium oxide powder to the skin, it is possible to obtain a light scattering effect due to a shape of the titanium oxide particles and thus it is possible to improve a feeling of transparency.

In general, in a case where the octahedral-shaped particles do not agglomerate with one another, the average particle diameter of the octahedral-shaped particles which is converted from the BET specific surface area is measured by making an observation with an electron microscope, and roughly matches an arithmetic average value of maximum values, the maximum value being a maximum value of line segments each of which connects two apexes which face each other in the octahedral-shaped particle.

Therefore, the fact that the value of (the average value of the maximum values/the BET-converted average particle diameter) is closer to 1.0 means that the titanium oxide particles are less likely to agglomerate with one another and more particles are present in a state of primary particles.

On the other hand, in a case where primary particles agglomerate with one another to form the octahedral-shaped particles, an arithmetic average value of maximum values which are measured by making an observation with an electron microscope and in which the maximum value is a maximum value of line segments each of which connects two apexes which face each other in the octahedral-shaped particle, does not match the average particle diameter of the octahedral-shaped particles which is converted from the BET specific surface area. Therefore, in a case where the primary particles agglomerate with one another to form the octahedral-shaped particles, the average value of the maximum values/the BET-converted average particle diameter is higher than 2.5.

(Crystalline Phase)

A crystalline phase (a crystalline structure) of the titanium oxide powder of the present embodiment is not particularly limited, and may be any one single phase of an anatase type, a rutile type, and a brookite type, or may be a mixed phase thereof. Among these, the crystalline phase of the titanium oxide powder of the present embodiment is preferably the anatase type.

A case where the crystalline phase of the titanium oxide powder is the anatase type is advantageous from the viewpoint that a concealing ability is further increased in a case where cosmetics containing the titanium oxide powder is applied to the skin, and a color which is close to a color of the human skin is obtained in a case of being mixed with a cosmetic base.

The fact that the titanium oxide powder has the anatase type can be confirmed by, for example, an X-ray diffractometer (trade name: X'Pert PRO, manufactured by Spectris Co., Ltd.). In a case where a measurement result by the X-ray diffractometer is an anatase single phase, a titanium oxide powder has the anatase type.

(Surface Treatment)

The titanium oxide powder or the titanium oxide particles of the present embodiment may have an inorganic compound or an organic compound on a surface thereof.

As a method of attaching the inorganic compound or the organic compound to the surface of the titanium oxide particles, for example, a method of performing a surface treatment using a surface treatment agent, and the like are mentioned.

The surface treatment agent is not particularly limited as long as the surface treatment agent can be used in cosmetics, and can be appropriately selected depending on a purpose. As the surface treatment agent, an inorganic component and an organic component are mentioned.

As the inorganic component, silica, alumina, and the like are mentioned.

As the organic component, for example, a silicone compound, an organopolysiloxane, a fatty acid, fatty acid soap, fatty acid ester, an organic titanate compound, a surfactant, a non-silicone compound, and the like are mentioned. One of these may be used alone, or two or more thereof may be used in combination.

As the silicone compound, for example, silicone oil such as methyl hydrogen polysiloxane, dimethyl polysiloxane, and methylphenyl polysiloxane; alkyl silane such as methyl trimethoxysilane, ethyl trimethoxysilane, hexyl trimethoxysilane, and octyl trimethoxysilane; fluoroalkyl silane such as trifluoromethylethyl trimethoxysilane and heptadecafluorodecyl trimethoxysilane; methicone, hydrogen dimethicone, triethoxysilyl ethyl polydimethylsiloxyethyl dimethicone, triethoxysilylethyl polydimethylsiloxyethylhexyl dimethicone, (acrylates/acrylic acid tridecyl/triethoxysilylpropyl methacrylate/dimethicone methacrylate) copolymer, triethoxycaprylyl silane, and the like are mentioned. In addition, the silicone compound may be a monomer of a compound or a copolymer thereof. One of these may be used alone, or two or more thereof may be used in combination.

As the fatty acid, for example, palmitic acid, isostearic acid, stearic acid, lauric acid, myristic acid, behenic acid, oleic acid, rosin acid, 12-hydroxystearic acid, and the like are mentioned.

As the fatty acid soap, for example, aluminum stearate, calcium stearate, aluminum 12-hydroxystearate, and the like are mentioned.

As the fatty acid ester, for example, dextrin fatty acid ester, cholesterol fatty acid ester, sucrose fatty acid ester, starch fatty acid ester, and the like are mentioned.

As the organic titanate compound, for example, isopropyl triisostearoyl titanate, isopropyl dimethacryl isostearoyl titanate, isopropyl tri(dodecyl) benzene sulfonyl titanate, neopentyl (diallyl)oxy-tri(dioctyl) phosphate titanate, neopentyl (diallyl)oxy-trineodododecanoyl titanate, and the like are mentioned.

According to the titanium oxide powder of the present embodiment, in a case where cosmetics containing the titanium oxide powder are applied to the skin, it is possible to obtain natural finish in which paleness peculiar to titanium oxide particles is decreased while achieving both a concealing ability and a feeling of transparency. Furthermore, in a case where the cosmetics containing the titanium oxide powder of the present embodiment are applied to the skin, spreadability and adhesion to the skin are excellent. Therefore, the titanium oxide powder of the present embodiment can be suitably used for cosmetics, and, in particular, can be suitably used for base makeup cosmetics.

[Method for Manufacturing Titanium Oxide Powder]

A method for manufacturing titanium oxide powder of the present invention has a first step of preparing a reaction solution by mixing a hydrolyzed product of a titanium alkoxide or a titanium metal salt with a compound having a five-membered ring that contains nitrogen, and subjecting this reaction solution to hydrothermal synthesis, to produce titanium oxide particles. In addition, the method for manufacturing titanium oxide powder of the present invention has, as necessary, a second step of mixing a reaction solution containing the titanium oxide particles which have been subjected to hydrothermal synthesis and are obtained in the first step with the same reaction solution as in the first step which have not been subjected to hydrothermal synthesis, and subjecting the mixture to hydrothermal synthesis. Furthermore, the method for manufacturing titanium oxide powder of the present invention has a step of drying the reaction solution obtained in the first step or the second step at 400° C. or lower.

(First Step)

The first step is a step of producing titanium oxide particles.

In the first step, the hydrolyzed product of titanium alkoxide or titanium metal salt is mixed with the compound having a five-membered ring that contains nitrogen to prepare a reaction solution, and this reaction solution is subjected to hydrothermal synthesis to produce titanium oxide particles.

(Hydrolyzed Product of Titanium Alkoxide or Titanium Metal Salt)

The hydrolyzed product of titanium alkoxide or titanium metal salt is obtained by hydrolyzing the titanium alkoxide or the titanium metal salt.

The hydrolyzed product is, for example, a cake-like solid which is a white solid, and is hydrated titanium oxide called metatitanic acid or orthotitanic acid.

As the titanium alkoxide, for example, tetraethoxytitanium, tetraisopropoxytitanium, tetra-n-propoxytitanium, tetra-n-butoxytitanium, and the like are mentioned. One of these may be used alone, or two or more thereof may be used in combination. Among these, tetraisopropoxytitanium and tetra-n-butoxytitanium are preferable, and tetraisopropoxytitanium is more preferable, from the viewpoint of easy availability and easy control of a hydrolysis rate.

As the titanium metal salt, for example, titanium tetrachloride, titanium sulfate, and the like are mentioned. One of these may be used alone, or two or more thereof may be used in combination.

In the present embodiment, in order to obtain high-purity anatase type titanium oxide particles, it is preferable to use a high purity titanium alkoxide or a high purity titanium metal salt.

The hydrolyzed product contains a by-product such as alcohols, hydrochloric acid, and sulfuric acid.

Since the by-product inhibits nucleation and crystal growth of titanium oxide particles, it is preferable to clean the hydrolyzed product with pure water.

As a method for cleaning the hydrolyzed product, for example, decantation, Nutsche method, ultrafiltration method, and the like are mentioned.

(Compound Having Five-Membered Ring that Contains Nitrogen)

The compound having a five-membered ring that contains nitrogen is contained in the reaction solution due to a function as a pH adjuster of the reaction solution and a function as a catalyst for hydrothermal synthesis.

As the compound having a five-membered ring that contains nitrogen, for example, pyrrole, imidazole, indole, purine, pyrrolidine, pyrazole, triazole, tetrazole, isothiazole, isoxazole, furazan, carbazole, 1,5-diazabicyclo-[4.3.0]-5-nonene, and the like are mentioned. One of these may be used alone, or two or more thereof may be used in combination.

Among these, as the compound having a five-membered ring that contains nitrogen, a compound containing one nitrogen atom is preferable from the viewpoint of narrowing a particle size distribution of titanium oxide powder and of further improving crystallinity. For example, pyrrole, indole, pyrrolidine, isothiazole, isoxazole, furazan, carbazole, and 1,5-diazabicyclo-[4.3.0]-5-nonene are preferable.

Among these, as the compound having a five-membered ring that contains nitrogen, a compound which contains one nitrogen atom and of which a five-membered ring has a saturated heterocyclic structure is more preferable from the viewpoint of narrowing a particle size distribution of titanium oxide powder and of further improving crystallinity. For example, pyrrolidine, and 1,5-diazabicyclo-[4.3.0]-5-nonene are more preferable.

A method for preparing the reaction solution is not particularly limited, and can be appropriately selected depending on a purpose. For example, a method of mixing by using a stirrer, a bead mill, a ball mill, an attritor, a dissolver, or the like, and the like are mentioned.

In addition, water may be added to the reaction solution so that a concentration of the reaction solution is adjusted. As the water to be added to the reaction solution, deionized water, distilled water, pure water, and the like are mentioned.

A pH of the reaction solution is preferably 9 or more and 13 or less, and more preferably 11 or more and 13 or less, from the viewpoint that a catalytic action of the compound having a five-membered ring that contains nitrogen appropriately functions and a nucleation rate becomes appropriate.

In a case where the pH of the reaction solution is in a range of 9 or more and 13 or less, production of titanium oxide particles and efficiency of crystal growth become better.

The pH of the reaction solution can be regulated by controlling a content of the compound having a five-membered ring that contains nitrogen.

A titanium atom concentration in the reaction solution can be appropriately selected depending on a size of target titanium oxide particles, and the titanium atom concentration is preferably 0.05 mol/L or more and 3.0 mol/L or less, and more preferably 0.5 mol/L or more and 2.5 mol/L or less.

In a case where the titanium atom concentration in the reaction solution is 0.05 mol/L or more and 3.0 mol/L or less, a nucleation rate becomes appropriate, so that production of titanium oxide particles and efficiency of crystal growth become better.

The titanium atom concentration in the reaction solution can be regulated by controlling a content of the hydrolyzed product of titanium alkoxide or titanium metal salt.

A molar ratio (titanium atom:compound having a five-membered ring that contains nitrogen) of titanium atoms to compounds having a five-membered ring that contains nitrogen in the reaction solution is preferably 1.0:0.01 to 1.0:2.0. In a case where the molar ratio of titanium atoms to compounds having a five-membered ring that contains nitrogen in the reaction solution is within the above-mentioned range, it is possible to produce titanium oxide particles having eight or more faces.

For example, in a case of producing star-shaped titanium oxide particles, a molar ratio of titanium atom:compound having a five-membered ring that contains nitrogen is preferably 1.0:0.01 to 1.0:1.0, and more preferably 1.0:0.1 to 1.0:0.7.

In addition, in a case of producing octahedral-shaped titanium oxide particles, a molar ratio of titanium atom:compound having a five-membered ring that contains nitrogen is preferably 1.0:0.5 to 1.0:2.0, and more preferably 1.0:0.6 to 1.0:1.8, and even more preferably 1.0:0.7 to 1.0:1.5.

Hydrothermal synthesis is a method in which a reaction solution is heated to allow titanium in the reaction solution to react in the presence of high-temperature and high-pressure hot water. A hydrothermal synthetic reaction is preferably carried out in a sealed container that can withstand high-temperature and high-pressure.

The hydrothermal synthesis is carried out by placing a reaction solution in a high-temperature and high-pressure container called an autoclave, sealing the autoclave, and heating the reaction solution together with the autoclave.

In a case where the reaction solution is heated, a pressure in the container rises due to evaporation of moisture in the reaction solution, which allows a high-temperature and high-pressure reaction to occur.

A heating and holding temperature in the hydrothermal synthesis is preferably 150° C. or more and 350° C. or less, and more preferably 150° C. or more and 210° C. or less.

In a case where the heating and holding temperature in hydrothermal synthesis is within the above-mentioned range, the hydrolyzed product of titanium alkoxide or titanium metal salt can have an improved solubility in water and can be dissolved in the reaction solution. In addition, the above case allows nuclei of titanium oxide particles to be produced and allows the nuclei to be grown, so that titanium oxide particles of a desired shape can be manufactured.

A heating rate in the hydrothermal synthesis is not particularly limited, and can be appropriately selected depending on a purpose.

A pressure in the hydrothermal synthesis is a pressure in a case where the reaction solution is heated to the above-mentioned temperature range in a high-temperature and high-pressure container.

During heating in the autoclave, it is preferable to stir the reaction solution using a stirring device.

A stirring speed is not particularly limited, and can be appropriately selected depending on a purpose. The stirring speed is preferably 100 rpm or more and 300 rpm or less.

A heating and holding time in the hydrothermal synthesis is not particularly limited, and can be appropriately selected depending on a size of the titanium oxide particles to be produced. The heating and holding time is preferably 3 hours or longer, and more preferably 4 hours or longer.

In a case where the heating and holding time is shorter than 3 hours, the hydrolyzed product of titanium alkoxide or titanium metal salt as a raw material may not react and a yield may decrease.

The heating and holding time is influenced by a type and a concentration of the raw material. Therefore, an appropriate preliminary experiment may be conducted, so that the hydrothermal synthesis is carried out for a heating and holding time which allows titanium oxide particles to have a desired size. For example, the heating and holding time may be 9 hours, 12 hours, 24 hours, 48 hours, or 72 hours. However, from the viewpoint of production efficiency, heating may be stopped at a time point where titanium oxide particles reach a desired size.

(Second Step)

The second step is a step of further crystal-growing the titanium oxide particles obtained in the first step. The second step is carried out in a case where a size of the titanium oxide particles obtained is smaller than a desired size.

The second step is a step of mixing a reaction solution containing the titanium oxide particles which have been subjected to hydrothermal synthesis and are obtained in the first step with the same reaction solution (the hydrolyzed product of titanium alkoxide or titanium metal salt, and the compound having a five-membered ring that contains nitrogen) as in the first step which have not been subjected to hydrothermal synthesis, and subjecting the mixture to hydrothermal synthesis.

A mixing ratio of the reaction solution containing the titanium oxide particles which have been subjected to hydrothermal synthesis and are obtained in the first step to the same reaction solution (the hydrolyzed product of titanium alkoxide or titanium metal salt, and the compound having a five-membered ring that contains nitrogen) as in the first step which have not been subjected to hydrothermal synthesis is preferably 1:1 to 1:20 in a case of being converted by mass of titanium oxide particles.

A hydrothermal synthesis in the second step can be carried out under the same conditions as in the first step.

In a case of growing the titanium oxide particles obtained in the second step, a reaction solution containing the titanium oxide particles which have been subjected to hydrothermal synthesis and are obtained in the second step may be mixed with the same reaction solution (the hydrolyzed product of titanium alkoxide or titanium metal salt, and the compound having a five-membered ring that contains nitrogen) as in the first step which have not been subjected to hydrothermal synthesis, and then may be subjected to hydrothermal synthesis under the same conditions as in the first step. In addition, the same steps may be repeated one or more times until titanium oxide particles having a desired size are obtained.

(Third Step)

A method of taking out the titanium oxide powder from the reaction solution after carrying out the first step or the second step is not particularly limited, and can be appropriately selected depending on a purpose. As the method of taking out the titanium oxide powder from the reaction solution, for example, a method of performing solid-liquid separation such as decantation and Nutsche method, and the like are mentioned.

After taking out the titanium oxide powder, the obtained titanium oxide powder may be cleaned with pure water or the like for the purpose of decreasing impurities.

The titanium oxide powder taken out by solid-liquid separation is heated at 400° C. or lower and dried.

The lower limit of the heating temperature of the titanium oxide powder is not particularly limited as long as the titanium oxide powder can be dried. For example, the heating temperature may be 200° C., may be 250° C., or may be 300° C.

The titanium oxide powder of the present embodiment can be obtained by taking out the titanium oxide powder from the reaction solution which has been subjected to hydrothermal synthesis and heating the titanium oxide powder at 400° C. or lower. The obtained titanium oxide powder can be stored by a preferred method selected as necessary. For example, it is preferable to store under a condition of room temperature (25 degrees) together with a desiccant.

The powder is usually stored at room temperature in an environment where water is not easily absorbed to the powder by using a desiccant or the like. Therefore, it is difficult to assume that a mass reduction rate changes due to storage. In a case where storage conditions are not appropriate and the measured mass reduction rate is too large due to, for example, water entering a storage container, the powder may be dried again at 400° C. or lower. After drying again, the mass reduction rate can be confirmed again.

It is also possible to subject the titanium oxide powder to a surface treatment. A timing of performing the surface treatment is not particularly limited, and can be appropriately selected depending on a purpose. As the timing of performing the surface treatment, for example, after the first step or after the second step, and the like are mentioned.

A method of performing the surface treatment is not particularly limited, and a known method can be appropriately selected depending on a type of a surface treatment agent to be used.

[Dispersion]

The dispersion of the present embodiment contains the titanium oxide powder of the present embodiment and a dispersion medium. The dispersion of the present embodiment contains other components as necessary.

The dispersion of the present embodiment may be in a low-viscosity liquid state or a high-viscosity paste state.

A content of the titanium oxide powder in the dispersion of the present embodiment is not particularly limited, and can be appropriately selected depending on a purpose. For example, the content of the titanium oxide powder may be 0.1% by mass or more and 90% by mass or less, 1% by mass or more and 80% by mass or less, 5% by mass or more and 70% by mass or less, 10% by mass or more and 60% by mass or less, or 20% by mass or more and 50% by mass or less, with respect to a total amount of the dispersion of the present embodiment.

(Dispersion Medium)

The dispersion medium is not particularly limited as long as the dispersion medium can be blended with cosmetics, and can be appropriately selected depending on a purpose. As the dispersion medium, for example, water, alcohols, esters, ethers, ketones, hydrocarbon, amides, polysiloxanes, modified polysiloxanes, hydrocarbon oil, ester oil, a higher fatty acid, higher alcohol, and the like are mentioned. One of these may be used alone, or two or more thereof may be used in combination.

As the alcohols, for example, methanol, ethanol, 1-propanol, 2-propanol, 1-butanol, 2-butanol, octanol, glycerin, and the like are mentioned.

As the esters, for example, ethyl acetate, butyl acetate, ethyl lactate, propylene glycol monomethyl ether acetate, propylene glycol monoethyl ether acetate, g-butyrolactone, and the like are mentioned.

As the ethers, for example, diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, diethylene glycol monoethyl ether, and the like are mentioned.

As the ketones, for example, acetone, methyl ethyl ketone, methyl isobutyl ketone, acetyl acetone, cyclohexanone, and the like are mentioned.

As the hydrocarbon, for example, aromatic hydrocarbon such as benzene, toluene, xylene, and ethylbenzene; cyclic hydrocarbon such as cyclohexane, and the like are mentioned.

As the amides, dimethylformamide, N,N-dimethylacetoacetamide, N-methylpyrrolidone, and the like are mentioned.

As the polysiloxanes, for example, chain-like polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexasiloxane, and the like are mentioned.

As the modified polysiloxanes, for example, an amino-modified polysiloxane, a polyether-modified polysiloxane, an alkyl-modified polysiloxane, a fluorine-modified polysiloxane, and the like are mentioned.

As the hydrocarbon oil, for example, liquid paraffin, squalane, isoparaffin, branched chain-like light paraffin, petrolatum, ceresin, and the like are mentioned.

As the ester oil, for example, isopropyl myristate, cetyl isooctanoate, glyceryl trioctanoate, and the like are mentioned.

As the higher fatty acid, for example, lauric acid, myristic acid, palmitic acid, stearic acid, and the like are mentioned.

As the higher alcohol, for example, lauryl alcohol, cetyl alcohol, stearyl alcohol, hexyl dodecanol, isostearyl alcohol, and the like are mentioned.

(Other Components)

The other components are not particularly limited as long as the components do not impair an effect of the dispersion of the present embodiment, and can be appropriately selected depending on a purpose. As the other components, for example, a dispersant, a stabilizer, a water-soluble binder, a thickener, an oil-soluble preservative, an ultraviolet absorber, an oil-soluble agent, oil-soluble coloring matters, oil-soluble proteins, a vegetable oil, an animal oil, and the like are mentioned. One of these may be used alone, or two or more thereof may be used in combination.

A content of the dispersion medium is not particularly limited, and can be appropriately selected depending on a purpose. A content of the dispersion medium is preferably 10% by mass or more and 99% by mass or less, more preferably 20% by mass or more and 90% by mass or less, and even more preferably 30% by mass or more and 80% by mass or less, with respect to a total amount of the dispersion of the present embodiment.

According to the dispersion of the present embodiment, in a case where cosmetics containing the dispersion of the present embodiment is applied to the skin, it is possible to obtain natural finish in which paleness peculiar to titanium oxide particles is decreased while achieving both a concealing ability and a feeling of transparency. Furthermore, in a case where the cosmetics containing the titanium oxide powder of the present embodiment are applied to the skin, spreadability and adhesion to the skin are excellent. Therefore, the dispersion of the present embodiment can be suitably used for cosmetics, and, in particular, can be suitably used for base makeup cosmetics.

[Method for Manufacturing Dispersion]

A method for manufacturing the dispersion of the present embodiment is not particularly limited, and a known method can be adopted. As the method for manufacturing the dispersion of the present embodiment, for example, a method of manufacturing a dispersion by mechanically dispersing the titanium oxide powder of the present embodiment with respect to a dispersion medium by a dispersing device, and the like are mentioned.

As the dispersing device, a stirrer, a self-revolution type mixer, a homomixer, an ultrasonic homogenizer, a sand mill, a ball mill, a roll mill, and the like are mentioned.

In a case of being applied to the skin, the dispersion of the present embodiment is capable of decreasing paleness peculiar to titanium oxide while achieving both a concealing ability and a feeling of transparency. Furthermore, in a case where the cosmetics containing the titanium oxide powder of the present embodiment are applied to the skin, spreadability and adhesion to the skin are excellent.

[Cosmetics]

The cosmetics of the present embodiment contain the titanium oxide powder of the present embodiment and a cosmetic base. The cosmetics of the present embodiment contain other components as necessary.

Any content of the titanium oxide powder in the cosmetics can be selected, but the content of the titanium oxide powder is preferably 0.1% by mass or more and 50% by mass or less, with respect to a total of the cosmetics. For example, the content of the titanium oxide powder may be 0.1% to 5% by mass, 5% to 15% by mass, 15% to 35% by mass, or 35% to 50% by mass.

(Cosmetic Base)

The cosmetic base can be appropriately selected from cosmetic bases usually used in cosmetics, and, for example, talc, mica, and the like are mentioned. One of these may be used alone, or two or more thereof may be used in combination.

A content of the cosmetic base in the cosmetics is not particularly limited, and can be appropriately selected depending on a purpose.

(Other Components)

In addition to the titanium oxide powder and the cosmetic base of the present embodiment, the cosmetics of the present embodiment can contain other components within a range which does not impair an effect of the present embodiment.

The other components can be appropriately selected from components usually used in cosmetics. As the other components, for example, a solvent, an oil agent, a surfactant, a humectant, an organic ultraviolet absorber, an antioxidant, a thickener, a fragrance, a colorant, a physiologically active component, an antibacterial agent, and the like are mentioned. One of these may be used alone, or two or more thereof may be used in combination.

A content of the other components in the cosmetics is not particularly limited, and can be appropriately selected depending on a purpose.

A method for manufacturing the cosmetics of the present embodiment is not particularly limited, and can be appropriately selected depending on a purpose. As the method for manufacturing the cosmetics of the present embodiment, for example, a manufacturing method in which the titanium oxide powder is mixed with the cosmetic base and the mixture is mixed with the other components, a manufacturing method in which the titanium oxide powder is mixed with existing cosmetics, a manufacturing method in which the dispersion is mixed with the cosmetic base and the mixture is mixed with the other components, and a manufacturing method in which the dispersion is mixed with existing cosmetics, and the like are mentioned.

(Form)

A form of the cosmetics of the present embodiment is not particularly limited, and can be appropriately selected depending on a purpose. As the form of the cosmetics of the present embodiment, for example, a powder-like form, powdery solid-like form, a solid-like form, a liquid-like form, a gel-like form, and the like are mentioned. In a case where the form of the cosmetics is liquid-like or gel-like, a dispersion form of the cosmetics is not particularly limited, and can be appropriately selected depending on a purpose. As the dispersion form of the gel-like cosmetics, for example, a water-in-oil type (W/O type) emulsion, an oil-in-water type (O/W type) emulsion, an oil type, and the like are mentioned.

As the cosmetics of the present embodiment, for example, base makeup, nail polish, lipstick, and the like are mentioned. Among these, the base makeup is preferable.

As the base makeup, for example, makeup base used mainly for decreasing irregularities of the skin, foundation used mainly for adjusting a color of the skin, face powder used mainly for improving fixation of foundation to the skin, and the like are mentioned.

According to the cosmetics of the present embodiment, it is possible to decrease paleness peculiar to titanium oxide particles while having a concealing ability and a feeling of transparency in a case of being applied to the skin. Furthermore, in a case where the cosmetics containing the titanium oxide powder of the present embodiment are applied to the skin, spreadability and adhesion to the skin are excellent.

EXAMPLES

Hereinafter, the present invention will be described more specifically with reference to Examples and Comparative Examples. However, the present invention is not limited to the following Examples.

Example 1

(Production of Titanium Oxide Powder)

1 L of pure water was placed in a glass container having a capacity of 2 L, and 1 mol of tetraisopropoxytitanium (trade name: A-1, manufactured by Nippon Soda Co., Ltd.) was added dropwise while performing stirring, to obtain a white suspension containing a hydrolyzed product of a titanium alkoxide.

Next, the white suspension was subjected to solid-liquid separation, to obtain a white cake (1 mol in terms of titanium oxide) which is a solid portion of the hydrolyzed product of titanium alkoxide.

Next, pyrrolidine (manufactured by Kanto Chemical Co., Inc.) in an amount of 0.7 mol and the obtained white cake were placed in an autoclave, and pure water was added to make a total amount 1 kg. The sealed container was held at 220° C. for 9 hours and hydrothermal synthesis was carried out to obtain a reaction solution containing the titanium oxide particles.

The reaction solution containing titanium oxide particles was subjected to solid-liquid separation and the solid was dried at 300° C., to obtain a titanium oxide powder of Example 1.

(Measurement of BET Specific Surface Area and Average Particle Diameter Converted from BET Specific Surface Area)

A BET specific surface area of the titanium oxide powder of Example 1 was measured using a specific surface area meter (trade name: BELSORP-mini, manufactured by Bel Japan, Inc.). As a result, the BET specific surface area of the titanium oxide powder of Example 1 was 13 $m^2/g$.

Furthermore, as described later, it was confirmed that an amount of the octahedral-shaped particles was 70% by number or more. An average particle diameter of the titanium oxide powder of Example 1 which is converted from a BET specific surface area was calculated by Expression (1). As a result, a BET-converted average particle diameter was 312 nm. The results are shown in Table 1.

BET-converted average particle diameter (nm)
    =16240/(BET specific surface area (m2/g)×ρ
    (g/cm3))    (1)

In Expression (1), ρ represents a density of the titanium oxide, and ρ=4 g/cm³.

(Measurement of Shape)

"Measurement of Line Segments Connecting Two Apexes which Face Each Other and Amount of Octahedral-Shaped Particles"

Figure 2:
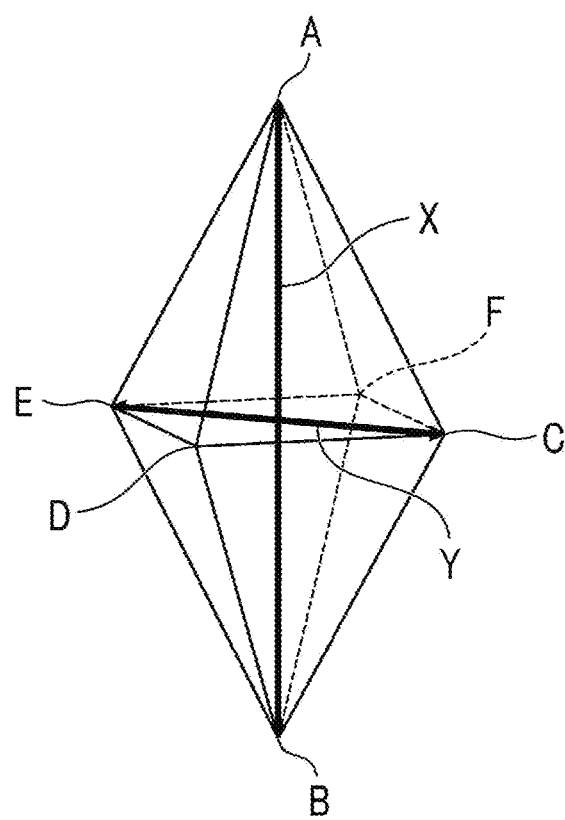
FIG. 2 is another schematic diagram showing a preferred example of octahedral-shaped titanium oxide particles.
Figure 3:
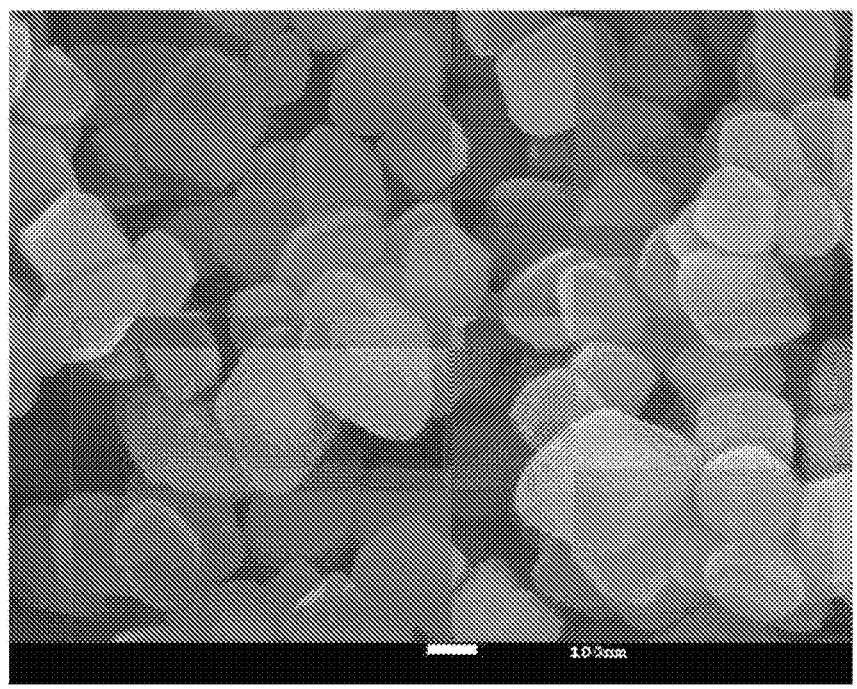
FIG. 3 is a view showing a scanning electron microscope image of titanium oxide particles of Example 1.

A maximum value (hereinafter indicated by (X)) of line segments each of which connects two apexes which face each other in each particle shown in FIG. 2, and a minimum value (hereinafter indicated by (Y)) of line segments, each of which is substantially orthogonal to a line segment which corresponds to the maximum value, and each of which connects two apexes which face each other, were measured with a scanning electron microscope (SEM) (trade name: S-4800, manufactured by Hitachi High-Technologies Corporation) by observing a secondary electron image of the titanium oxide particles of Example 1. The SEM image is shown in FIG. 3.

100 octahedral-shaped particles included in the titanium oxide particles of Example 1 were observed, and an average value of the above (X), an average value of the above (Y), and an average value of ratios (X/Y) of the X to the Y were calculated. As a result, the average value of the (X) was 350 nm, a value (hereinafter referred to as "average value of (X)/BET-converted average particle diameter" in some cases) obtained by dividing the average value of the (X) by the BET-converted average particle diameter was 1.1, and the average value of the ratios (X/Y) was 2.0.

In addition, as a result of observing 100 titanium oxide particles with a scanning electron microscope, 70% by number of octahedral-shaped titanium oxide particles were present in the titanium oxide powder. The results are shown in Table 1.

"Identification of Shape of Titanium Oxide Particles"

Figure 4:
FIG. 4 is a view showing a transmission electron microscope image of the titanium oxide particles of Example 1.

The titanium oxide powder of Example 1 was observed with a transmission electron microscope (TEM) (model number: H-800, manufactured by Hitachi High-Technologies Corporation). The TEM image is shown in FIG. 4. Also in a TEM image, it was confirmed that the octahedral-shaped titanium oxide particles were contained. The results are shown in Table 1.

(Identification of Crystalline Phase of Titanium Oxide Particles)

A crystalline phase of the titanium oxide powder of Example 1 was identified using an X-ray diffractometer (trade name: X'PertPRO, manufactured by Spectris Co., Ltd.). As a result, the titanium oxide powder of Example 1 was in an anatase single phase. The results are shown in Table 1.

(Measurement of Mass Reduction Rate)

10 g of the titanium oxide powder obtained in Example 1 was fired at 800° C. for 1 hour in an electric furnace (model number: KDF-S70, manufactured by DENKEN.Co.ltd.), and a mass reduction rate (%) before and after calcination was measured ((mass before calcination−mass after calcination)/mass before calcination×100). As a result, the mass reduction rate of the titanium oxide powder of Example 1 was 0.08%. The results are shown in Table 1.

"Production of Cosmetics"

2 g of the titanium oxide powder of Example 1 and 8 g of talc were mixed with each other to produce base makeup cosmetics of Example 1.

(Evaluation of Adhesion)

Each of the obtained base makeup cosmetics of Example 1 was applied on a 5 cm square substrate (trade name: HELIOPLATE HD-6, manufactured by Helioscreen) so as to be 12 mg to 14 mg, to produce applied substrates.

The mass of the obtained coated applied substrate was measured.

Next, the applied surface of the applied substrate was faced down and horizontally fixed by hand at a position 10 cm from a floor.

Next, the applied substrate was allowed to freely fall from a height of 10 cm, the mass of the applied substrate after falling was measured, and a mass change rate (%) ((mass of applied substrate before falling−mass of applied substrate after falling)/mass of applied substrate before falling×100) was calculated.

This mass change rate was used as an index of the adhesion. Since a smaller mass change rate indicates a higher adhesion, it is preferable that the value is smaller.

The mass change rate of each of the base makeup cosmetics of Example 1 was 98%. The results are shown in Table 1.

(Evaluation of spreadability)

Each of the base makeup cosmetics of Example 1 was applied by 1 mg each on a 5 cm square substrate (trade name: HELIOPLATE HD-6, manufactured by Helioscreen). It was visually confirmed whether the entire surface of the substrate was covered with the base makeup cosmetics, and an amount of the base makeup cosmetics required to cover the entire surface was measured.

The amount of base makeup cosmetics required to cover the entire surface of the substrate was used as an index of spreadability. Since a smaller amount of the base makeup cosmetics required to cover the entire surface of the substrate indicates a higher spreadability, it is preferable that the value is smaller.

The amount of the base makeup cosmetics of Example 1 required to cover the entire surface of the substrate was 9 mg. The results are shown in Table 1.

(Evaluation of paleness, feeling of transparency, and concealing ability)

Each of the base makeup cosmetics of Example 1 was applied on a 5 cm square substrate (trade name: HELIOPLATE HD-6, manufactured by Helioscreen) so as to be 12 mg to 14 mg, to produce applied substrates.

For each of the applied substrates, diffuse transmission spectrum (TT), diffuse reflection spectrum (TR), and linear reflection spectrum (R) were measured using a spectrophotometer (model number; UV-3150, manufactured by Shimadzu Corporation), and evaluation was performed using the following indices. In each case, an incident direction of light was measured from an applied surface, and the reflection spectrum was measured on the basis of a molded plate obtained by compressing barium sulfate powders (special grade, manufactured by Kanto Chemical Co., Inc.).

The results are shown in Table 2.

A ratio ($TR_{450nm}/TR_{550nm}$) of a diffuse reflectance ($TR_{450nm}$) at 450 nm to a diffuse reflectance ($TR_{550nm}$) at 550 nm was used as an index for paleness. Since it can be said as being paler as the ratio becomes larger than 1, it is preferable that the value of $TR_{450nm}/TR_{550nm}$ is smaller.

A correlation between the index for paleness and an appearance viewed by human's eyes is shown in Table 3.

(Feeling of Transparency)

A ratio ($R_{550nm}/TR_{550nm}$) of a linear reflectance ($R_{550nm}$) at 550 nm and the diffuse reflectance ($TR_{550nm}$) at 550 nm was used as an index for feeling of transparency. Since a smaller ratio indicates a higher feeling of transparency, it is preferable that the value is smaller. A correlation between the index for feeling of transparency and an appearance viewed by human's eyes is shown in Table 3.

(Concealing Ability)

The diffuse reflectance ($TR_{550nm}$) at 550 nm was used as an index for concealing ability. In a case where the diffuse reflectance is large, it can be said that the concealing ability is large. Thus, it is preferable that the value is large.

A correlation between the index for concealing ability and an appearance viewed by human's eyes is shown in Table 3.

Example 2

100 g (8 g of titanium oxide) of a reaction solution containing the titanium oxide particles obtained in the production process of Example 1, the white cake (1 mol (80 g) in terms of titanium oxide) obtained in the production process of Example 1, and 0.7 mol of pyrrolidine were placed in an autoclave, and pure water was added to make a total amount to 1 kg. The resultant was stirred to produce a mixed solution.

Next, the container was sealed, and the mixed solution was held at 220° C. for 9 hours to crystal-grow the titanium oxide particles, so that a reaction solution containing the titanium oxide particles was obtained.

Next, the obtained reaction solution containing the titanium oxide particles was subjected to solid-liquid separation and the solid was dried at 300° C., to obtain a titanium oxide powder of Example 2.

With regard to the obtained titanium oxide powder of Example 2, a BET specific surface area, a shape, a crystalline phase, a mass reduction rate were measured in the same manner as in Example 1.

As a result, the BET specific surface area was 9 m²/g, and a BET-converted average particle diameter was 451 nm. An average value of (X) in the octahedral-shaped titanium oxide particles is 450 nm, the average value of the (X)/the BET-converted average particle diameter was 1.0, and an average value of ratios (X/Y) was 2.0. The results are shown in Table 1.

In addition, in the titanium oxide particles of Example 2, octahedral-shaped titanium oxide particles were 65% by number with respect to an entirety of the particles, and a crystalline phase of the titanium oxide powder was in an anatase single phase. The results are shown in Table 1. In addition, the mass reduction rate of the titanium oxide powder of Example 2 was 0.06%.

Base makeup cosmetics of Example 2 were obtained in the same manner as in Example 1 except that the titanium oxide powder of Example 2 was used instead of the titanium oxide powder of Example 1.

In the same manner as in Example 1, adhesion (mass change rate), spreadability (amount of base makeup cosmetics required to cover the entire surface of the substrate), paleness, a feeling of transparency, and a concealing ability were evaluated. The results are shown in Table 2.

Example 3

A titanium oxide powder of Example 3 and base makeup cosmetics of Example 3 were obtained in the same manner as in Example 2, except that the reaction solution containing the titanium oxide powder was subjected to solid-liquid separation, and then the solid was dried at 400° C. instead of 300° C.

With regard to the obtained titanium oxide powder of Example 3, a BET specific surface area, a shape, a crystalline phase, a mass reduction rate were measured in the same manner as in Example 1.

As a result, the BET specific surface area was 6 m²/g, and a BET-converted average particle diameter was 677 nm. An average value of (X) in the octahedral-shaped titanium oxide particles was 740 nm, the average value of the (X)/the BET-converted average particle diameter was 1.1, and an average value of ratios (X/Y) was 2.0. The results are shown in Table 1.

In addition, in the titanium oxide particles of Example 3, octahedral-shaped titanium oxide particles were 60% by number with respect to an entirety of the particles, and a crystalline phase of the titanium oxide powder was in an anatase single phase. The results are shown in Table 1.

In addition, the mass reduction rate of the titanium oxide powder of Example 3 was 0.04%. The results are shown in Table 1.

In addition, in the same manner as in Example 1, adhesion, spreadability, paleness, a feeling of transparency, and a concealing ability of the base makeup cosmetics of Example 3 were evaluated. The results are shown in Table 2.

Comparative Example 1

A titanium oxide powder of Comparative Example 1 and base makeup cosmetics of Comparative Example 1 were obtained in the same manner as in Example 1, except that the reaction solution containing the titanium oxide powder was subjected to solid-liquid separation, and the solid was dried at 500° C. instead of 300° C.

With regard to the obtained titanium oxide powder of Comparative Example 1, a BET specific surface area, a shape, a crystalline phase, a mass reduction rate were measured in the same manner as in Example 1.

As a result, the BET specific surface area was 12 m²/g, and a BET-converted average particle diameter was 338 nm. An average value of (X) in the octahedral-shaped titanium oxide particles was 330 nm, the average value of the (X)/the BET-converted average particle diameter was 1.0, and an average value of ratios (X/Y) was 2.0. The results are shown in Table 1.

In addition, in the titanium oxide particles of Comparative Example 1, octahedral-shaped titanium oxide particles were 70% by number with respect to an entirety of the particles, and a crystalline phase of the titanium oxide powder was in an anatase single phase. The results are shown in Table 1.

In addition, the mass reduction rate of the titanium oxide powder of Comparative Example 1 was 0.02%.

In addition, in the same manner as in Example 1, adhesion, spreadability, paleness, a feeling of transparency, and a concealing ability of the base makeup cosmetics of Comparative Example 1 were evaluated. The results are shown in Table 2.

Comparative Example 2

A titanium oxide powder of Comparative Example 2 and base makeup cosmetics of Comparative Example 2 were obtained in the same manner as in Example 1, except that the reaction solution containing the titanium oxide powder was subjected to solid-liquid separation, and the solid was dried at 700° C. instead of 300° C.

With regard to the obtained titanium oxide powder of Comparative Example 2, a BET specific surface area, a shape, a crystalline phase, a mass reduction rate were measured in the same manner as in Example 1.

As a result, the BET specific surface area was 10 m²/g, and a BET-converted average particle diameter was 406 nm. An average value of (X) in the octahedral-shaped titanium oxide particles was 420 nm, the average value of the (X)/the BET-converted average particle diameter was 1.0, and an average value of ratios (X/Y) was 2.0. The results are shown in Table 1.

In addition, in the titanium oxide particles of Comparative Example 2, octahedral-shaped titanium oxide particles were 70% by number with respect to an entirety of the particles, and a crystalline phase of the titanium oxide powder was in an anatase single phase. The results are shown in Table 1.

In addition, the mass reduction rate of the titanium oxide powder of Comparative Example 2 was 0.01%. The results are shown in Table 1.

In addition, in the same manner as in Example 1, adhesion, spreadability, paleness, a feeling of transparency, and a concealing ability of the base makeup cosmetics of Comparative Example 2 were evaluated. The results are shown in Table 2.

Comparative Example 3

Commercially available titanium oxide particles having an average diameter of 300 nm and having a spherical-shaped rutile type with a BET specific surface area of 6 m²/g were used as titanium oxide particles of Comparative Example 3.

In addition, a BET-converted average particle diameter was calculated by Expression (2). Since the particles are spherical, Expression (2) different from Expression (1) was used for calculation. As a result, the BET-converted average particle diameter was 250 nm, and a value obtained by dividing the average particle diameter by the BET-converted average particle diameter was 1.2.

$$\text{BET-converted average particle diameter (nm)}=6000/(\text{BET specific surface area (m}^2\text{/g)}\times\rho\text{ (g/cm}^3\text{))} \quad (2)$$

In Expression (2), $\rho$ represents a density of titanium oxide, and therefore, $\rho=4$ g/cm³.

An average particle diameter of spherical-shaped particles which is converted from a BET specific surface area roughly matches an average diameter of primary particles.

In addition, in the titanium oxide particles of Comparative Example 3, an average value of (X) is 300 nm, the average value of the (X)/the BET-converted average particle diameter was 1.2, and an average value of ratios (X/Y) was 1.0. The results are shown in Table 1. Since each of the titanium oxide particles having a spherical shape, a diameter of sphere was used as the values of (X) and (Y).

In the spherical-shaped titanium oxide particles, a diameter at a predetermined position corresponds to a maximum value (X) of line segments each of which connects two apexes which face each other in each particle. In the spherical-shaped titanium oxide particles, another diameter which is substantially orthogonal to the diameter at a predetermined position corresponds to a minimum value (Y) of line segments, each of which is substantially orthogonal to a line segment which corresponds to the maximum value (X), and each of which connects two apexes which face each other.

In addition, in the titanium oxide particles of Comparative Example 3, an amount of octahedral-shaped titanium oxide particles was 0% by number with respect to an entirety of the particles. The results are shown in Table 1.

Base makeup cosmetics of Comparative Example 3 were obtained in the same manner as in Example 1 except that the titanium oxide powder of Comparative Example 3 was used instead of the titanium oxide powder of Example 1.

In the same manner as in Example 1, paleness, a feeling of transparency, and a concealing ability were evaluated. The results are shown in Table 2.

Comparative Example 4

Commercially available titanium oxide particles were used as a titanium oxide powder of Comparative Example 4.

The titanium oxide particles, of which primary particles are a spheroid having an average major diameter of 100 nm and an average minor diameter of 30 nm and the primary particles agglomerate with one another to form a spindle shape with an average major diameter (average major diameter at agglomeration) of 300 nm, an average minor diameter (average minor diameter at agglomeration) of 136 nm, and an average value of the major diameter at agglomeration/the minor diameter at agglomeration of 2.2, and which are a rutile type with a BET specific surface area of 21 m²/g, were used.

Since a primary particle shape is a spheroid, the BET-converted average particle diameter was determined using Expression (3) different from Expression (1). Specifically, P=50 nm (100 nm/2) and Q=3.33 (100/30) were calculated using Expression (3). As a result, the BET-converted average particle diameter was 100 nm.

$$\text{BET specific surface area (m}^2\text{/g)}=1000\times(1+P/((1-(1-(1/Q)^2))^{1/2}\times P\times(1-(1/Q)^2)^{1/2}\times\sin^{-1}((1-(1/Q)^2)^{1/2}))/(2\times\rho\times P/3) \quad (3)$$

In Expression (3), $\rho$ represents a density of the titanium oxide, and $\rho=4$ g/cm³.

In addition, in Expression (3), P represents a radius (nm) of the average major diameter of the spheroid which is the primary particles, and Q represents an average value of aspect ratios obtained by dividing a radius of a long axis (major diameter of primary particles/2) by a radius of a short axis (minor diameter of primary particles/2).

In addition, in the titanium oxide particles of Comparative Example 4, an average value of (X) is 300 nm, the average value of the (X)/the BET-converted average particle diameter was 3.0, and an average value of ratios (X/Y) was 2.2. The results are shown in Table 1.

The spindle-shaped titanium oxide particles of Comparative Example 4 agglomerate with one another. Therefore, the average major diameter (average major diameter at agglomeration) corresponds to the maximum value (X) and the average minor diameter (average minor diameter at agglomeration) which is substantially orthogonal to a line segment which corresponds to the maximum value (X) corresponds to the minimum value (Y).

The value obtained by dividing the major diameter at agglomeration by the BET-converted average particle diameter was 3.0. The results are shown in Table 1.

Since the titanium oxide particles of Comparative Example 4 agglomerate with one another, a major diameter of an agglomerate and an average particle diameter converted from the BET specific surface area deviate from each other, and as a result, the major diameter of the agglomerate/the BET-converted average particle diameter is greater than 2.5.

In addition, in the titanium oxide particles of Comparative Example 4, an amount of octahedral-shaped titanium oxide particles was 0% by number with respect to an entirety of the particles. The results are shown in Table 1.

Base makeup cosmetics of Comparative Example 4 were obtained in the same manner as in Example 1 except that the titanium oxide powder of Comparative Example 4 was used instead of the titanium oxide powder of Example 1.

In the same manner as in Example 1, paleness, a feeling of transparency, and a concealing ability were evaluated. The results are shown in Table 2.

Comparative Example 5

A titanium oxide powder of Comparative Example 5 was obtained in the same manner as in Example 1 except that the resultant was held at 220° C. for 3 hours in place of being held at 220° C. for 9 hours in Example 1.

With regard to the obtained titanium oxide powder of Comparative Example 5, a BET specific surface area, a shape, and a crystalline phase were measured in the same manner as in Example 1.

As a result, the BET specific surface area was 22 m$^2$/g, and a BET-converted average particle diameter was 185 nm. An average value of (X) in the octahedral-shaped titanium oxide particles was 220 nm, the average value of the (X)/the BET-converted average particle diameter was 1.2, and an average value of ratios (X/Y) was 2.0. The results are shown in Table 1.

In addition, in the titanium oxide powder of Comparative Example 5, an amount of octahedral-shaped titanium oxide particles was 70% by number with respect to an entirety of the particles, and the crystalline phase of the titanium oxide particles was in an anatase single phase.

The results are shown in Table 1.

Base makeup cosmetics of Comparative Example 5 were obtained in the same manner as in Example 1 except that the titanium oxide powder of Comparative Example 5 was used instead of the titanium oxide powder of Example 1.

In the same manner as in Example 1, paleness, a feeling of transparency, and a concealing ability were evaluated. The results are shown in Table 2.

Comparative Example 6

100 g (8.8 g of titanium oxide) of a reaction solution containing the titanium oxide particles obtained in the production process of Example 2, the white cake (1 mol (80 g) in terms of titanium oxide) obtained in the production process of Example 1, and 0.7 mol of pyrrolidine were placed in an autoclave, and pure water was added to make a total amount to 1 kg. The resultant was stirred to produce a mixed solution.

Next, the container was sealed, and the mixed solution was held at 220° C. for 9 hours to obtain a reaction solution containing the titanium oxide particles.

Next, 100 g (8.8 g of titanium oxide) of a reaction solution containing the titanium oxide particles, the white cake (1 mol (80 g) in terms of titanium oxide) obtained in the production process of Example 1, and 0.7 mol of pyrrolidine were placed in an autoclave. Furthermore, pure water was added to the autoclave to make a total amount to 1 kg, and the resultant was stirred to produce a mixed solution.

Next, the container was sealed, and the mixed solution was held at 220° C. for 9 hours to obtain a reaction solution containing the titanium oxide particles.

Next, the obtained reaction solution containing the titanium oxide particles was subjected to solid-liquid separation and dried at 200° C., to obtain a titanium oxide powder of Comparative Example 6.

With regard to the obtained titanium oxide powder of Comparative Example 6, a BET specific surface area, a shape, and a crystalline phase were measured in the same manner as in Example 1.

As a result, the BET specific surface area was 4 m$^2$/g, and a BET-converted average particle diameter was 1015 nm. An average value of (X) in the octahedral-shaped titanium oxide particles was 1200 nm, the average value of the (X)/the BET-converted average particle diameter was 1.2, and an average value of ratios (X/Y) was 2.0.

In addition, in the titanium oxide powder of Comparative Example 6, an amount of octahedral-shaped titanium oxide particles was 65% by number, and the crystalline phase of the titanium oxide powder was in an anatase single phase.

Base makeup cosmetics of Comparative Example 6 were obtained in the same manner as in Example 1 except that the titanium oxide powder of Comparative Example 6 was used instead of the titanium oxide powder of Example 1.

In the same manner as in Example 1, paleness, a feeling of transparency, and a concealing ability were evaluated. The results are shown in Table 2.

Comparative Example 7

Commercially available titanium oxide particles having an average diameter of 500 nm and having a spherical-shaped rutile type with a BET specific surface area of 4 m$^2$/g were used as a titanium oxide powder of Comparative Example 7.

With respect to the titanium oxide powder of Comparative Example 7, a BET-converted average particle diameter was calculated in the same manner as in Comparative Example 1, and as a result, the BET-converted average particle diameter was 375 nm. In addition, the value obtained by dividing the average diameter by the BET-converted average particle diameter was 1.3.

In addition, in the titanium oxide powder of Comparative Example 7, an average value of (X) is 500 nm, the average value of the (X)/the BET-converted average particle diameter was 1.3, and an average value of ratios (X/Y) was 1.0. In the spherical-shaped titanium oxide particles, a diameter at a predetermined position corresponds to a maximum value (X) of line segments each of which connects two apexes which face each other in each particle. In the spherical-shaped titanium oxide particles, another diameter which is substantially orthogonal to the diameter at a predetermined position corresponds to a minimum value (Y) of line segments, each of which is substantially orthogonal to a line segment which corresponds to the maximum value (X), and each of which connects two apexes which face each other.

In addition, in the titanium oxide powder of Comparative Example 7, an amount of octahedral-shaped titanium oxide particles was 0% by number.

Base makeup cosmetics of Comparative Example 7 were obtained in the same manner as in Example 1 except that the titanium oxide powder of Comparative Example 7 was used instead of the titanium oxide powder of Example 1.

In the same manner as in Example 1, paleness, a feeling of transparency, and a concealing ability were evaluated. The results are shown in Table 2.

By comparing Examples 1 to 3 with Comparative Example 1 and Comparative Example 2, it was confirmed that the titanium oxide powder having a mass reduction rate of 0.03% by mass or more and 0.5% by mass or less have excellent spreadability and adhesion.

In addition, by comparing Examples 1 to 3 with Comparative Examples 3 to 7, it was confirmed that the titanium oxide powder having a specific surface area of 5 m²/g or more and 15 m²/g or less and containing the polyhedral-shaped titanium oxide particles having eight or more faces can decrease paleness peculiar to titanium oxide while achieving both a concealing ability and a feeling of transparency. Therefore, it was clarified that the titanium oxide powder of the present embodiment is suitable for cosmetics for base makeup.

In order to confirm that the octahedral-shaped titanium oxide particles are capable of scattering light over a wide range, the following simulation was performed.

Figure 5:
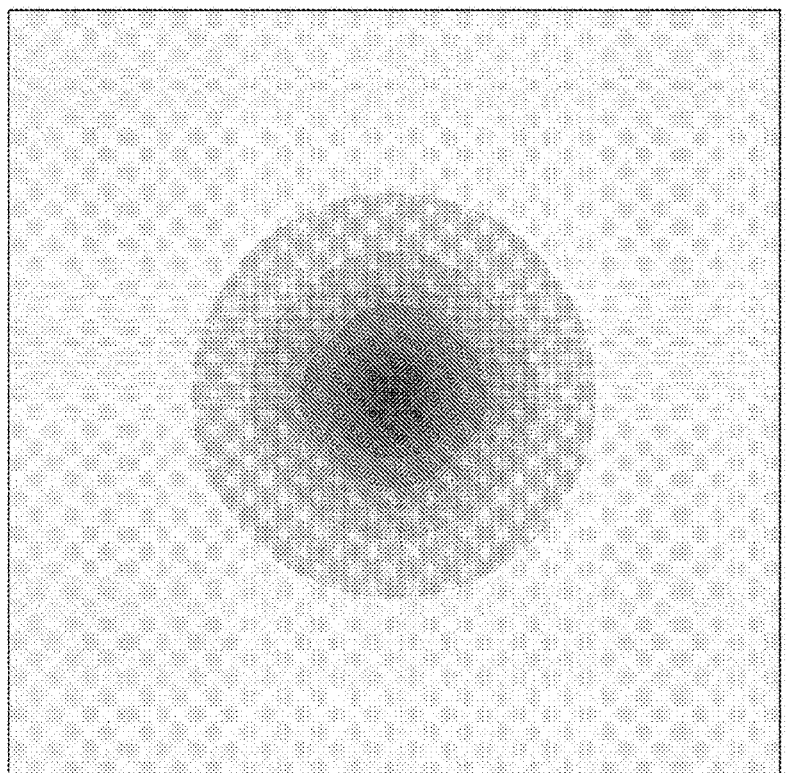
FIG. 5 is a view showing a result of simulating how light scatters in a case where spherical-shaped titanium oxide particles are irradiated with light.

In a case where each of spherical-shaped titanium oxide particles having a diameter of 500 nm and octahedral-shaped titanium oxide particles in which a maximum value of distances between two apexes which face each other in each particle is 500 nm is irradiated with light having a wavelength of 700 nm, simulation was performed by the Finite-difference time-domain (FDTD) method on how the light scatters. The simulation results on the spherical-shaped titanium oxide particles are shown in FIG. 5. In addition, the simulation results on the octahedral-shaped titanium oxide particles are shown in FIG. 6.

Figure 6:
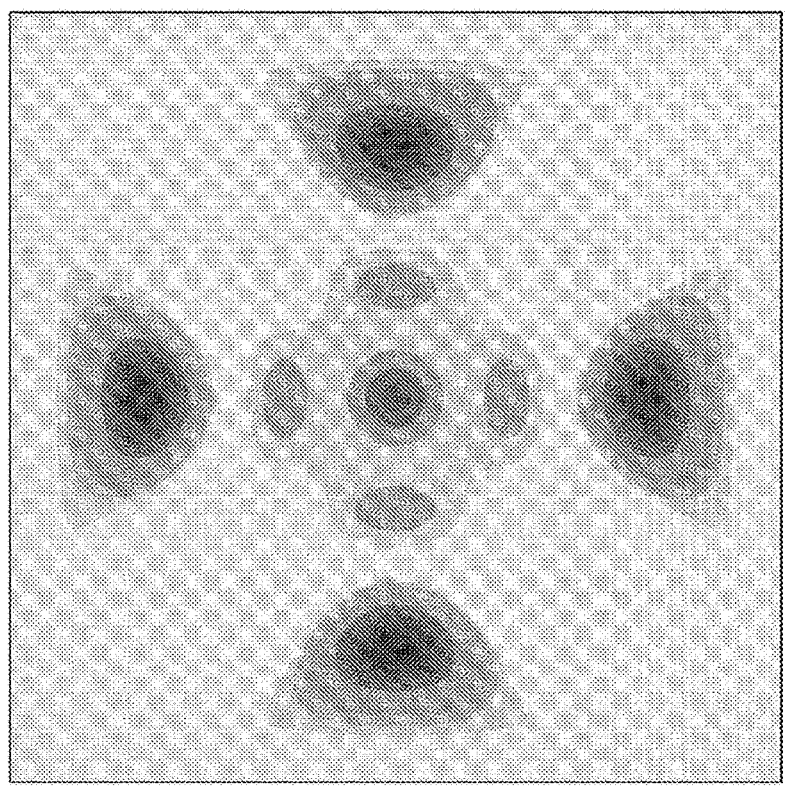
FIG. 6 is a view showing a result of simulating how light scatters in a case where octahedral-shaped titanium oxide particles are irradiated with light.

In FIGS. 5 and 6, it is assumed that the titanium oxide particles are present in a center of a square-shaped display surface. Therefore, in this simulation, it can be said that a degree of light scattering is large in a case where the light scattered when the titanium oxide particles present in the center are irradiated with light spreads larger (wider) in the display surface. On the other hand, in this simulation, it can be said that a degree of scattering is small in a case where the light with which the titanium oxide particles present in the center are irradiated does not spread or spreads small in the display surface.

TABLE 1

| | Drying temperature (° C.) | Shape | Crystalline phase | BET specific surface area (m²/g) | BET-converted average particle diameter (nm) | Maximum value (X) (nm) | Maximum value (X)/ (BET-converted average particle diameter) | Maximum value (X)/ Minimum value (Y) | % by number | Mass reduction rate (%) | Adhesion (%) | Spreadability (mg) |
|---|---|---|---|---|---|---|---|---|---|---|---|---|
| Example 1 | 300 | Octahedral shape | Anatase | 13 | 312 | 350 | 1.1 | 2.0 | 70 | 0.08 | 98 | 9 |
| Example 2 | 300 | Octahedral shape | Anatase | 9 | 451 | 450 | 1.0 | 2.0 | 65 | 0.06 | 97 | 9 |
| Example 3 | 400 | Octahedral shape | Anatase | 6 | 677 | 740 | 1.1 | 2.0 | 60 | 0.04 | 97 | 9 |
| Comparative Example 1 | 500 | Octahedral shape | Anatase | 12 | 338 | 330 | 1.0 | 2.0 | 70 | 0.02 | 81 | 13 |
| Comparative Example 2 | 700 | Octahedral shape | Anatase | 10 | 406 | 420 | 1.0 | 2.0 | 70 | 0.01 | 52 | 14 |
| Comparative Example 3 | — | Spherical shape | Rutile | 6 | 250 | 300 | 1.2 | 1.0 | 0 | — | — | — |
| Comparative Example 4 | — | Spindle shape | Rutile | 21 | 100 | 300 | 3.0 | 2.2 | 0 | — | — | — |
| Comparative Example 5 | 200 | Octahedral shape | Anatase | 22 | 185 | 220 | 1.2 | 2.0 | 70 | — | — | — |
| Comparative Example 6 | 200 | Octahedral shape | Anatase | 4 | 1015 | 1200 | 1.2 | 2.0 | 65 | — | — | — |
| Comparative Example 7 | — | Spherical shape | Rutile | 4 | 375 | 500 | 1.3 | 1.0 | 0 | — | — | — |

TABLE 2

| | Paleness | Feeling of transparency | Concealing ability |
|---|---|---|---|
| Example 1 | 1.02 | 0.01 | 48 |
| Example 2 | 1.01 | 0.01 | 50 |
| Example 3 | 1.01 | 0.02 | 53 |
| Comparative Example 1 | 1.02 | 0.01 | 49 |
| Comparative Example 2 | 1.02 | 0.02 | 51 |
| Comparative Example 3 | 1.03 | 0.05 | 48 |
| Comparative Example 4 | 1.13 | 0.02 | 42 |
| Comparative Example 5 | 1.07 | 0.02 | 42 |
| Comparative Example 6 | 1.01 | 0.04 | 63 |
| Comparative Example 7 | 1.01 | 0.04 | 58 |

TABLE 3

| | Value | Appearance viewed by human's eyes |
|---|---|---|
| Paleness $TR_{450\,nm}/TR_{550\,nm}$ | Lower than 1.05 | There is no paleness |
| | 1.05 or higher and lower than 1.10 | There is a little paleness |
| | 1.10 or higher | There is paleness |
| Feeling of transparency $R_{550\,nm}/TR_{550\,nm}$ | Lower than 0.03 | There is a feeling of transparency |
| | 0.03 or higher and lower than 0.05 | There is not much a feeling of transparency |
| | 0.05 or higher | There is no feeling of transparency |
| Concealing ability $TR_{550\,nm}$ | 45 or higher | There is a concealing ability |
| | 40 or higher and lower than 45 | There is not much a concealing ability |
| | Lower than 40 | There is no concealing ability |

From the results in FIGS. 5 and 6, it was confirmed that the octahedral-shaped titanium oxide particles scatter light up to an about 2 times longer distance than the spherical-shaped titanium oxide particles. Such results show that by making the particles an octahedral shape, it is possible to scatter light over a wide range and to achieve both a concealing ability and a feeling of transparency.

INDUSTRIAL APPLICABILITY

The titanium oxide powder of the present invention has a BET specific surface area of 5 $m^2/g$ or more and 15 $m^2/g$ or less, contains polyhedral-shaped titanium oxide particles having eight or more faces, is capable of decreasing paleness peculiar to titanium oxide particles while having a concealing ability and a feeling of transparency in a case of being applied to the skin, and has excellent spreadability on the skin and excellent adhesion to the skin since a mass reduction rate in a case of being heated at 800° C. for 1 hour in an air atmosphere is 0.03% by mass or more and 0.5% by mass or less. Therefore, the titanium oxide powder can be suitably used for base makeup cosmetics such as foundations. Furthermore, since the titanium oxide powder of the present invention has excellent performance as a white pigment, the titanium oxide powder can be used for industrial applications such as white ink and is thus industrially valuable.

The invention claimed is:

1. A population of titanium oxide particles having a BET specific surface area of 5 $m^2/g$ or more and 15 $m^2/g$ or less,
    wherein the population of titanium oxide particles comprises polyhedral-shaped titanium oxide particles having eight or more faces, and
    wherein the population of titanium oxide particles has a mass reduction rate in a case of being heated at 800° C. for 1 hour in an air atmosphere is 0.03% by mass or more and 0.5% by mass or less.

2. The population of titanium oxide particles according to claim 1,
    wherein the polyhedral-shaped titanium oxide particles are octahedral-shaped titanium oxide particles, in which each of the octahedral-shaped particles has line segments each of which connects two apexes which face each other and has a maximum value of the line segments, and an average value of the maximum values is 300 nm or higher and 1000 nm or lower.

3. The population of titanium oxide particles according to claim 2,
    wherein a ratio of the average value of the maximum values of the line segments to a BET-converted average particle diameter is 0.5 or higher and 2.5 or lower.

4. The population of titanium oxide particles according to claim 1,
    wherein an amount of the polyhedral-shaped titanium oxide particles in the population of titanium oxide particles is 50% by number or more.

5. The population of titanium oxide particles according to claim 1,
    wherein the population of titanium oxide particles has any one of an inorganic compound and an organic compound on a surface of the particle, and the mass reduction rate is calculated excluding the inorganic compound and the organic compound.

6. A dispersion, comprising:
    the population of titanium oxide particles according to claim 1; and
    a dispersion medium.

7. Cosmetics comprising:
    the population of titanium oxide particles according to claim 1; and
    a cosmetic base.

8. The population of titanium oxide particles according to claim 1,
    wherein a polyhedral shape having eight or more faces is an octahedral shape in which two congruent rectangular pyramids share a rectangular bottom surface, and
    the population of titanium oxide particles contains 60% by number or more of the octahedral-shaped titanium oxide particles.

9. The population of titanium oxide particles according to claim 2,
    wherein each of the octahedral-shaped particles has a rectangular bipyramidal shape in which two congruent rectangular pyramids share a rectangular bottom surface, and
    a tip end part of the rectangular bipyramid has any one of a sharp shape, a rounded shape, and a flat shape.

* * * * *